(12) United States Patent
Oh (10) Patent No.: US 9,050,104 B2
(45) Date of Patent: Jun. 9, 2015

(54) MAGNETICALLY-COUPLED BIPOLAR RADIOFREQUENCY ABLATION CATHETER

(75) Inventor: Seil Oh, Seoul (KR)

(73) Assignee: SEOUL NATIONAL UNIVERSITY HOSPITAL, Seoul (KR)

( * ) Notice: Subject to any disclaimer, the term of this patent is extended or adjusted under 35 U.S.C. 154(b) by 967 days.

(21) Appl. No.: 12/995,247

(22) PCT Filed: Feb. 9, 2010

(86) PCT No.: PCT/KR2010/000805
§ 371 (c)(1),
(2), (4) Date: Nov. 30, 2010

(87) PCT Pub. No.: WO2010/107182
PCT Pub. Date: Sep. 23, 2010

(65) Prior Publication Data
US 2011/0087210 A1    Apr. 14, 2011

(30) Foreign Application Priority Data
Mar. 19, 2009    (KR) .................. 10-2009-0023529

(51) Int. Cl.
| A61B 18/12 | (2006.01) |
|---|---|
| A61B 18/14 | (2006.01) |
| A61B 17/00 | (2006.01) |
| A61B 18/00 | (2006.01) |
| A61B 19/00 | (2006.01) |

(52) U.S. Cl.
CPC ......... *A61B 18/1492* (2013.01); *A61B 18/1206* (2013.01); *A61B 2017/00243* (2013.01); *A61B 2018/00577* (2013.01); *A61B 2018/00875* (2013.01); *A61B 2018/1467* (2013.01); *A61B 2019/2253* (2013.01)

(58) Field of Classification Search
CPC ................ A61B 18/1492; A61B 2017/00243; A61B 2018/0057; A61B 2018/1467; A61B 2019/2253
USPC ................................................. 606/27, 34, 41
See application file for complete search history.

(56) References Cited

U.S. PATENT DOCUMENTS

| 5,429,131 | A | * | 7/1995 | Scheinman et al. .......... 600/374 |
| 5,492,538 | A | | 2/1996 | Johlin, Jr. |
| 5,542,938 | A | | 8/1996 | Avellanet et al. |
| 5,954,665 | A | | 9/1999 | Ben-Haim |
| 6,524,303 | B1 | | 2/2003 | Garibaldi |
| 8,048,072 | B2 | * | 11/2011 | Verin et al. ....................... 606/41 |

(Continued)

OTHER PUBLICATIONS

International Search Report and Written Opinion issued in PCT/KR2010/000805 and dated Sep. 15, 2010.

*Primary Examiner* — Michael Peffley
*Assistant Examiner* — Daniel Fowler
(74) *Attorney, Agent, or Firm* — Lucas & Mercanti, LLP (57) ABSTRACT

The present invention provides a bipolar radiofrequency ablation catheter comprising a working catheter and a magnetic catheter. The magnetic catheter comprises a first tube; a magnet; a first electrode; and a first electrode connector, and the working catheter comprises a second tube; a metallic element; a second electrode; and a second electrode connector. According to the present invention, it is possible to create transmural lesions more completely and easily at a thick myocardial region such as left ventricle in which a transmural lesion could not be easily created by using conventional radiofrequency ablation catheters and thus it is expected to increase the treatment efficiency for tachycardia such as ventricular tachycardia and atrial fibrillation.

18 Claims, 8 Drawing Sheets

(56) References Cited

U.S. PATENT DOCUMENTS

| | | |
|---|---|---|
| 2004/0260273 A1 | 12/2004 | Wan |
| 2005/0187545 A1* | 8/2005 | Hooven et al. ............... 606/41 |
| 2005/0234444 A1 | 10/2005 | Hooven |
| 2006/0030844 A1 | 2/2006 | Knight et al. |
| 2006/0106375 A1* | 5/2006 | Werneth et al. ............... 606/32 |
| 2007/0179493 A1* | 8/2007 | Kim ............................. 606/33 |
| 2007/0255273 A1* | 11/2007 | Fernandez et al. ............ 606/41 |
| 2008/0132829 A1 | 6/2008 | Sansoucy |

\* cited by examiner

MAGNETICALLY-COUPLED BIPOLAR
RADIOFREQUENCY ABLATION CATHETER

CROSS-REFERENCE TO RELATED APPLICATIONS

This application is a national stage application of, and claims priority to, International Application No. PCT/KR2010/000805 filed 9 Feb. 2010, and also claims priority to Korean Patent Application No. 10-2009-0023529, filed 19 Mar. 2009.

FIELD OF THE INVENTION

The present invention relates to a radiofrequency catheter ablation, and more particularly to a radiofrequency ablation catheter for treating tachycardia.

BACKGROUND OF THE INVENTION

A catheter is a tubular apparatus for drawing liquid from a body cavity or cavities of organs. A cardiac catheterization is a procedure to insert a flexible catheter into a blood vessel (artery or vein) and reach to heart. The cardiac catheterization is used to inject medicine, measure blood pressure and blood flow of heart and central blood vessel, or diagnose a congenital heart disease. In addition, the procedure is used to investigate a narrowed passage between atrium and ventricle, and abnormal blood flow, or insert electrodes into heart to restore or control heartbeat. A left cardiac catheterization is recently developed and it is a very difficult and dangerous procedure because it is performed by inserting a catheter into artery in opposite direction of blood flow or puncturing interatrial septum; however, it is a very important diagnosing method.

The radiofrequency catheter ablation is a method to treat tachycardia by using electricity. This method is advantageous in that tachycardia can be treated without heart surgery. The radiofrequency catheter ablation is used to treat supraventricular tachycardia with pulse rate exceeding 100 BPM (beats per minute) and some ventricular tachycardia. Especially, it is very efficient to treat paroxysmal supraventricular tachycardia, ventricular tachycardia, atrial fibrillation, and atrial flutter. It has been mostly used to treat paroxysmal supraventricular tachycardia and recently it is increasingly used for atrial fibrillation The radiofrequency catheter ablation is a method in which radiofrequency electric currents emitted from an electrode catheter located at heart causes local tissue necrosis and finally removes a source area of tachycardia. In this method, when the radiofrequency electric current is released to an especially designed electrode catheter contacting with a lesion to be ablated, the end of the electrode is heated to 60° C.-100° C. and this heat causes heart tissue necrosis, finally removes irregular heartbeat. Specifically, this procedure is done on an empty stomach condition and three or four electrode catheters are inserted into a left or right groin region, accessing a femoral artery or a femoral vein under local anesthesia. An additional electrode catheter may be inserted into subclavian vein, if necessary. Through the electrode catheters, electric stimuli are given to several regions of heart and arrhythmia is caused to diagnose its mechanism and a source area. An injection may be used when arrhythmia is not caused, and the electrotherapy is repeatedly performed changing regions to be treated until source areas of tachycardia are ablated and tachycardia is not caused. Usually, the procedure is done 1-10 times and each procedure takes 3-5 hours. The success rate of treating paroxysmal supraventricular tachycardia is over 90%, and that of treating atrial fibrillation is 70-80%. In 5% of patients, complications such as atrioventricular conduction block, hemopericardium, myocardial infarction, embolism, thrombosis, and hemorrhage may occur. Further, there is a possibility of death. Atrioventricular conduction block can be treated by artificial pacemaker surgery, and embolism and thrombosis can be treated by emergency surgery to remove blood or thrombus. There is a chance to recur in 5% of patients even when the procedure is successfully performed.

The radiofrequency catheter ablation is performed by using a radiofrequency ablation catheter which ablates a source myocardial region of arrhythmia through radiofrequency electric currents. However, conventional radiofrequency ablation catheters create transmural lesions incompletely. Especially, it is so difficult to create a transmural lesion at a thick myocardial region such as left ventricle that the treatment efficiency for ventricular tachycardia or atrial fibrillation is low.

SUMMARY OF THE INVENTION

To solve the above-mentioned problems, the object of the present invention is to provide a magnetically-coupled bipolar radiofrequency ablation catheter to create transmural lesions completely and easily at thick myocardial regions.

In one embodiment of the invention, there is provided a bipolar radiofrequency ablation catheter comprising a working catheter and a magnetic catheter. The magnetic catheter comprises a first tube; a magnet; a first electrode; and a first electrode connector, and the working catheter comprises a second tube; a metallic element; a second electrode; and a second electrode connector.

In another embodiment of the invention, there is provided a bipolar radiofrequency ablation catheter comprising as follows: (a) a magnetic catheter which comprises a flexible hollow first tube, a magnet arranged in the inner side of the first tube in a row at regular intervals along longitudinal direction of the first tube, a first electrode attached to the outer surface of the first tube in a row at regular intervals along longitudinal direction of the first tube, and a first electrode connector connected to each first electrode by an electric wire arranged in the first tube; and (b) a working catheter which comprises a flexible hollow second tube, a metallic element arranged in the inner side of the second tube in a row at regular intervals along longitudinal direction of the second tube, a second electrode attached to the outer surface of the second tube in a row at regular intervals along longitudinal direction of the second tube, and a second electrode connector connected to each second electrode by an electric wire arranged in the second tube.

In another embodiment of the invention, there is provided a bipolar radiofrequency ablation catheter comprising as follows: (a) a magnetic catheter which comprises a flexible hollow first tube, an electromagnet arranged in the inner side of the first tube in a row at regular intervals along longitudinal direction of the first tube, a first electrode attached to the outer surface of the first tube in a row at regular intervals along longitudinal direction of the first tube, a first electrode connector connected to each first electrode by an electric wire arranged in the first tube, and an electromagnet connector connected to each electromagnet by an electric wire arranged in the first tube and finally connected to a magnetic controller to control on/off of the electromagnet; and (b) a working catheter which comprises a flexible hollow second tube, a metallic element arranged in the inner side of the second tube in a row at regular intervals along longitudinal direction of the second tube, a second electrode attached to the outer surface of the second tube in a row at regular intervals along longitudinal direction of the second tube, and a second electrode connector connected to each second electrode by an electric wire arranged in the second tube.

The present invention makes it possible to increase the success rate to treat the region in which a transmural lesion could not be easily created by using conventional radiofrequency ablation catheters. Specifically, according to the present invention, two electrodes of the magnetic catheter and the working catheter are pulled each other by magnetic force, and thus, it increases adhesive force to the myocardial tissue to be treated, finally, large transmural lesions are created. Therefore, the catheter of the present invention makes it possible to create transmural lesions more completely and easily at a thick myocardial region such as left ventricle in comparison with conventional radiofrequency ablation catheters. Further, it is expected to increase the treatment efficiency for tachycardia such as ventricular tachycardia and atrial fibrillation.

DESCRIPTION OF REFERENCE NUMERALS IN THE DRAWINGS

100: magnetic catheter
110: first tube
120: magnet
130: first electrode
140: first electrode connector
141: electric wire to connect first electrode and first electrode connector
150: electromagnet connector
151: electric wire to connect electromagnet and electromagnet connector
200: working catheter
210: second tube
220: metallic element
230: second electrode
240: second electrode connector
241: electric wire to connect second electrode and second electrode connector 300: radiofrequency generator
400: magnetic controller

DETAILED DESCRIPTION OF THE INVENTION

The present invention relates to a bipolar radiofrequency ablation catheter comprising a magnetic catheter and a working catheter. In the following, the present invention is described in detail through embodiments and referring to the attached drawings.

Figure 1:
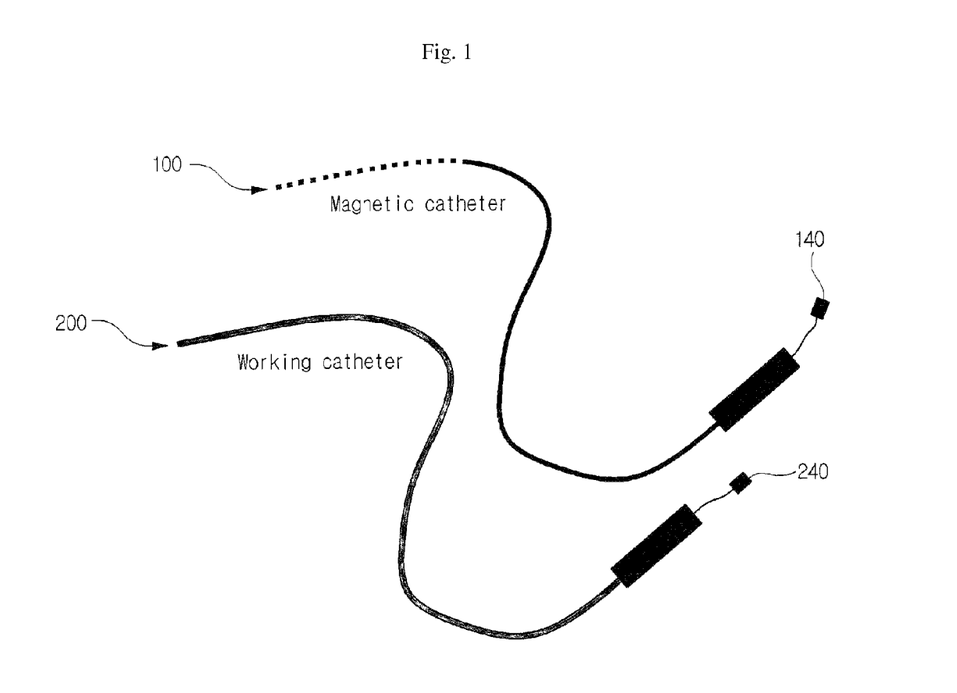
FIG. 1 is an exemplary view illustrating an overall structure of the bipolar radiofrequency ablation catheter according to the present invention.
Figure 2:
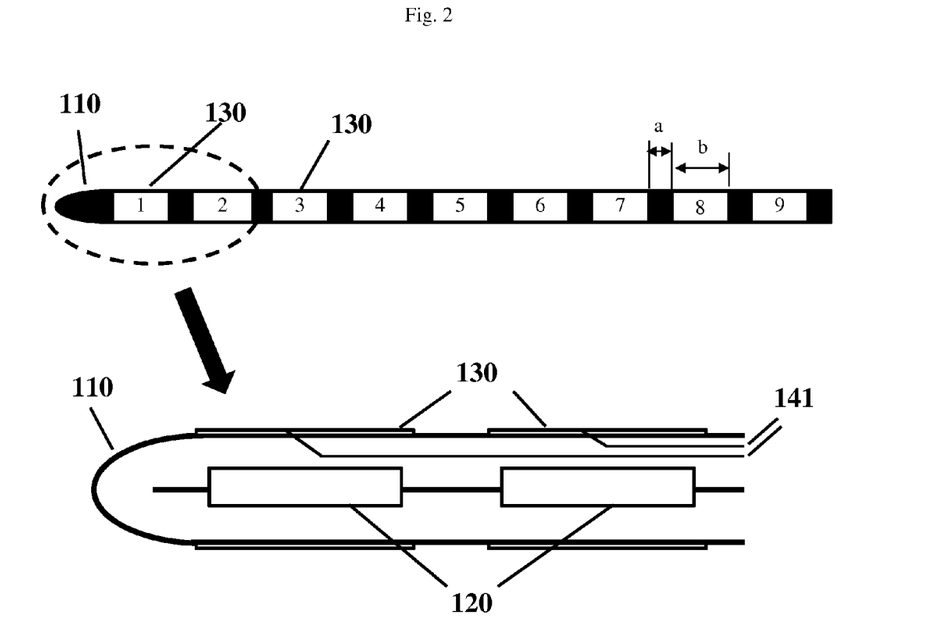
FIG. 2 is an exemplary view illustrating a detailed structure of the magnetic catheter according to the present invention.
Figure 3:
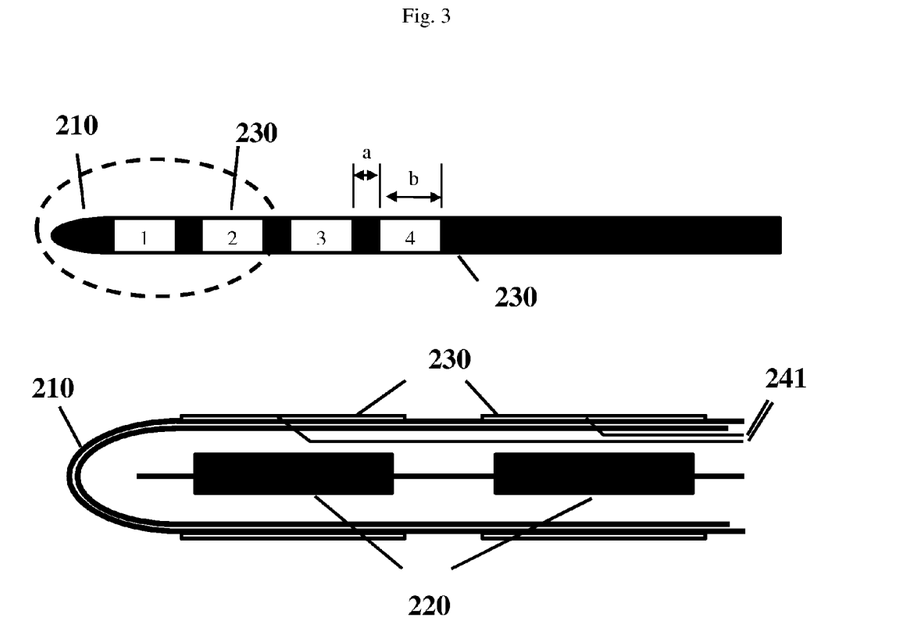
FIG. 3 is an exemplary view illustrating a detailed structure of the working catheter according to the present invention.

FIG. 1 shows one embodiment of the bipolar radiofrequency ablation catheter according to the present invention, which comprises a magnetic catheter (100) and a working catheter (200). FIG. 2 and FIG. 3 show the detailed structure of the magnetic catheter (100) and the working catheter (200).

As shown in FIG. 1 and FIG. 2, the magnetic catheter (100) comprises a first tube (110), a magnet (120), a first electrode (130), and a first electrode connector (140). As shown in FIG. 1 and FIG. 3, the working catheter (200) comprises a second tube (210), a metallic element (220), a second electrode (230), and a second electrode connector (240).

In the bipolar radiofrequency ablation catheter according to the present invention, the magnetic catheter (100) creates a pair with the working catheter (200), and the first electrode (130) of the magnetic catheter (100) interacts with the second electrode (230) of the working catheter (200). It is called as "bipolar" in that the two electrodes, the first (130) and the second (230), are acting simultaneously.

Figure 4:
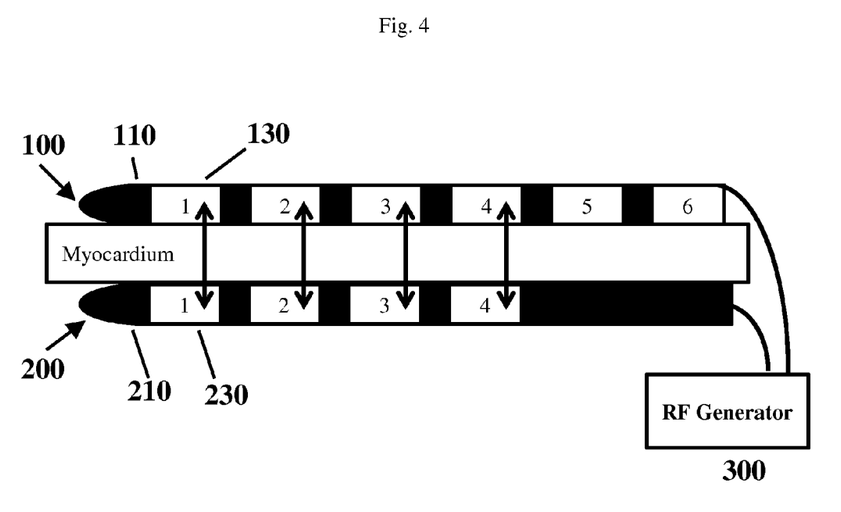
FIG. 4 is an exemplary view illustrating a circuit interconnection and operating principle of the bipolar radiofrequency ablation catheter according to the present invention.

As shown in FIG. 4, the catheter of the present invention creates transmural lesions by pressing myocardium between the magnetic catheter (100) and the working catheter (200), and releasing radiofrequency electric currents.

Specifically, the magnet (120) in the magnetic catheter (100) interacts with the metallic element (220) in the working catheter (200) by magnetic force produced by the magnet (120) in the magnetic catheter (100). Further, the first electrode (130) in the magnetic catheter (100) and the second electrode (230) in the working catheter (200) pulls each other, finally, the magnetic catheter (100) and the working catheter (200) press each other. In other words, the catheter of the present invention is characterized in that the working catheter (200) is pulled toward the magnetic catheter (100) by magnetic force produced by the magnet (120) in the magnetic catheter (100) and thus adhesive force to myocardial tissue is increased. The stronger adhesive force to myocardial tissue makes it possible to create larger transmural lesions more easily. Therefore, the present invention using magnetic force can create transmural lesions more easily at a thick myocardial region such as left ventricle in comparison with the conventional unipolar or bipolar catheter, finally, the success rate to treat atrial fibrillation and ventricular tachycardia is increased. As shown in FIG. 2 of the detailed structure of the magnetic catheter (100), the magnetic (120) may be arranged in the inner side of the first tube (110) and the first electrode (130) may be arranged on the outer side of the first tube (110).

The first tube (110) may be a hollow tube made of a flexible material, and the tube may freely be bent to adjust. Any kind of magnet, such as a permanent magnet or an electromagnet, can be used in the present invention.

As shown in FIG. 2, more than one magnet (120) may be arranged in a row at regular intervals along longitudinal direction of the first tube (100). There is no limitation on the number, size, and arranged interval of the magnet (120). However, the conditions in which the magnet arrangement does not obstruct the curve adjustment of the first tube (100) and magnetic force produced by the magnet (120) sufficiently affects the working catheter (200), are preferred. To satisfy this purpose in the arrangement of magnets, several small magnetic elements may be connected by a thin and flexible string or thread.

Furthermore, in order to affect the corresponding metallic element (220) sufficiently using the magnetic force produced by one magnet (120), it is recommended that the number, size, and arranged interval of magnets (120) be the same to those of metallic elements (220) of the working catheter (200).

Besides the above-mentioned arrangement of magnets, a person skilled in the art would find that any other arrangements of the magnet (120) are allowed to achieve the purpose of the present invention.

As shown in FIG. 2, more than one first electrode (130) may be attached to the outer surface of the first tube (110) with covering the tube (110) face, and the first electrode (130) may be arranged in a row at regular intervals along longitudinal direction of the first tube (100).

This arrangement of more than one first electrode (130) in a separate create is not to obstruct the curve adjustment of the first tube (110) when several electrodes (130) are arranged to the outer surface of the first tube (110). In other words, the arrangement of more than one first electrode (130) in a row at regular intervals along longitudinal direction of the first tube (110) does not obstruct to bend the flexible first tube (110).

Referring to FIG. 3 and FIG. 4, the first electrode (130) of the magnetic catheter (100) works with the second electrode (230) of the working catheter (200) to create transmural lesions with contacting the myocardial tissue to be treated. As shown in FIG. 4, radiofrequency electric currents produced by a radiofrequency generator (300) input to the first electrode (130) and it is heated to 70° C.-100° C., therefore, the heat destroys the myocardial tissue to create transmural lesions in a moment.

There is no limitation on the number, size, and arranged interval of the first electrode (130), however, it is desirable to arrange the first electrode (130) to work efficiently. The number, size, and arranged interval of the first electrode (130) may be determined by the result of preclinical trial. In order to create transmural lesions on the region to be treated without gap, the preferable size and arranged interval of the first electrode (130) is 10 mm and 4 mm respectively (see FIG. 2). Any other size and arranged interval of the first electrode (130) may be available, however, too bigger size (b) and too smaller arranged interval (a) of the first electrode (130) may obstruct the curve adjustment of the first tube (110).

On the contrary to this, transmural lesions with gap could be created when the size is below 10 mm and the arranged interval is above 4 mm. The preferable number of the first electrode (130) to perform the procedure more easily is 12 or more.

The magnetic catheter (100) may comprise a connector (140) for the first electrode (see FIG. 1). The first electrode connector (140) is connected to each electrode (130) by an electric wire (141) arranged in the first tube (1 10) of the magnetic catheter (see FIG. 2), finally, connected to the radiofrequency generator (300) when the procedure is performed (see FIG. 4).

The function of the first electrode connector (140) is to input radiofrequency electric currents produced by the radiofrequency generator (300) to the first electrode (130) of the magnetic catheter (100) and transfer the electric signal produced by the first electrode (130) into the radiofrequency generator (300). Thus, it is possible to cheek whether transmural lesions are successfully created by analyzing the electric signal (for example, impedance) recorded on the radiofrequency generator (300).

Figure 5:
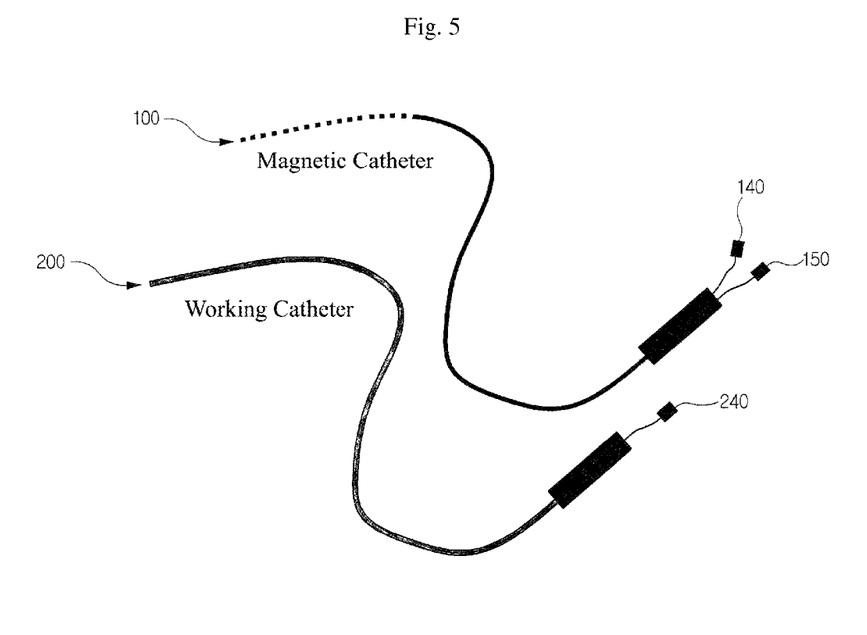
FIG. 5 is an exemplary view illustrating an overall structure of the bipolar radiofrequency ablation catheter according to the present invention when electromagnets are used.
Figure 6:
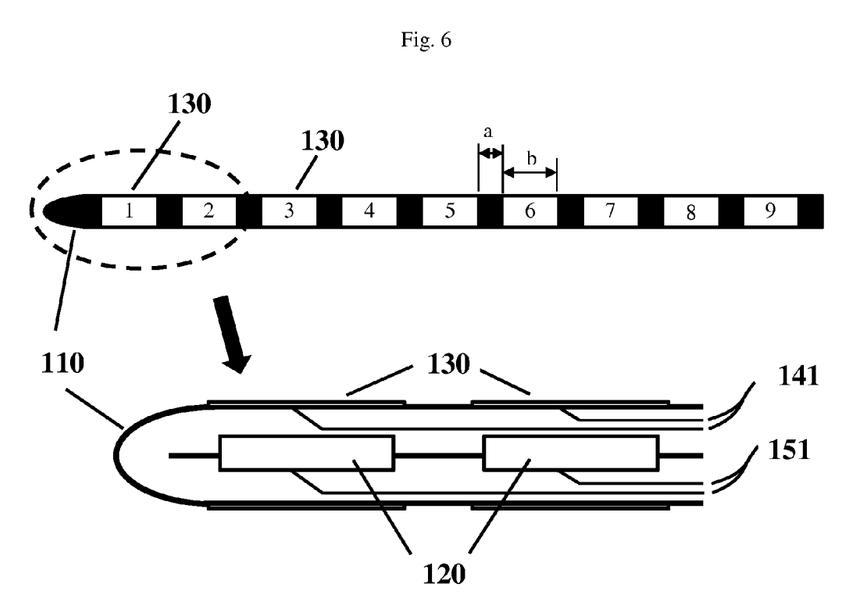
FIG. 6 is a view exemplary illustrating a detailed structure of the magnetic catheter according to the present invention when electromagnets are used.

As one embodiment of the present invention, an electromagnet may be used as a magnet (120) in the magnetic catheter (100). FIG. 5 shows the overall structure of the present invention when the electromagnet is used and FIG. 6 shows the detailed structure of the magnetic catheter (100) when the electromagnet is used. Further, FIG. 7 shows the circuit interconnection and operating principle of the present invention when the electromagnet is used.

Figure 7:
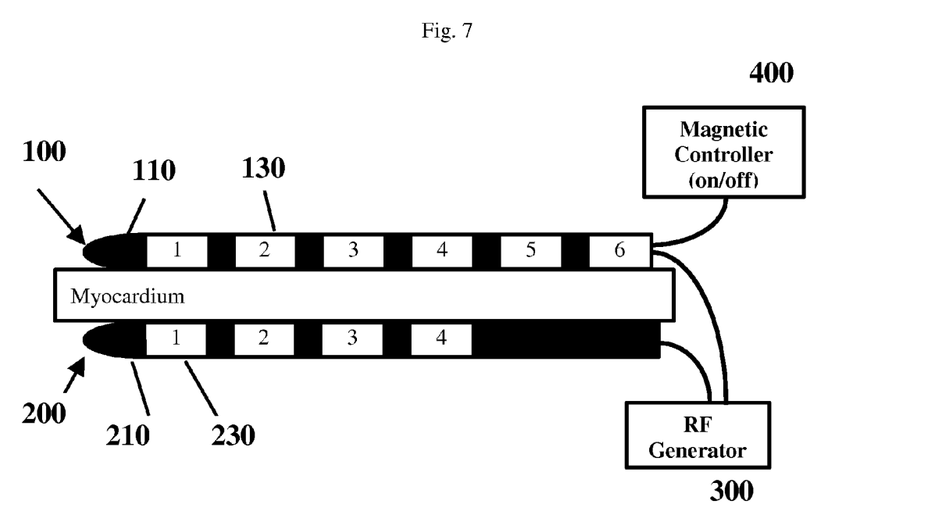
FIG. 7 is an exemplary view illustrating a circuit interconnection and operating principle of the bipolar radiofrequency ablation catheter according to the present invention when electromagnets are used.

Referring to FIG. 7, the electromagnet in the magnetic catheter (100) produces/exhausts magnetic force by on/off of electric currents from a magnetic controller (400). Specifically, the working catheter (200) is pulled and pressed into the magnetic catheter (100) when magnetic force is produced, while the magnetic catheter (100) and the working catheter (200) are separated when magnetic force is exhausted.

When the electromagnet is used, the magnetic catheter (100) may additionally comprise a connector (150) for electromagnets (see FIG. 5), and an electric wire (151) to connect the connector (150) with electromagnets (see FIG. 6). Specifically, the connector (150) is connected to each electromagnet by the electric wire (151) arranged in the first tube of the magnetic catheter, finally connected to the magnetic controller (400) when the procedure is performed (see FIG. 7). Thus, the electromagnet (120) is connected to the magnetic controller (400) by the connector (150). The magnetic controller (400) is a kind of apparatus for electric control with a switching function. The electric currents to the electromagnet are provided/blocked through the connector (150) by switching on/off the controller (400), therefore, magnetic force by the electromagnet are produced/exhausted.

Meanwhile, FIG. 3 shows the detailed structure of the working catheter (200). As shown in FIG. 3, the working catheter (200) may comprise a second tube (210), a metallic element (220), a second electrode (230), and a connector (240) for the second electrode. The second tube (210) of the working catheter (200) may be a hollowed tube made of a flexible material, and the tube may he bent freely to adjust. The metallic element (220) may be arranged in the inner side of the second tube (210) and the second electrode (230) may be arranged on the outer side of the second tube (210).

As shown in FIG. 3, more than one metallic element (220) may be arranged in a row at regular intervals along longitudinal direction of the second tube (210). The metallic element (220) is a slice made of metallic material and it adheres to a magnet. Thus, the metallic element (220) is pulled toward the magnet (120) by magnetic force produced by the magnet (120) in the magnetic catheter (100), finally the magnetic catheter (100) and the working catheter (200) press each other.

There is no limitation on the kind, number, size, and arranged interval of the metallic element (220). However, the conditions in which the metallic element (220) does not obstruct the curve adjustment of the second tube (210) of the working catheter (200) and magnetic force produced by the magnet (120) sufficiently affects the metallic element (220), are preferred. In order not to obstruct the curve adjustment of the second tube (210) in the arrangement of metallic elements (220), several small metallic elements (220) may be connected by a thin and flexible string or thread (see FIG. 3). Further, in order magnetic force produced by one magnet (120) to affect the corresponding metallic element (220) sufficiently, it is recommended that the number, size, and arranged interval of metallic elements (220) be the same to those of magnets (120) of the magnetic catheter (100) (see FIG. 4). FIG. 4 shows one embodiment of the circuit interconnection and operating principle of the bipolar radiofrequency ablation catheter according to the present invention.

Besides the above-mentioned arrangement of metallic elements, it is obvious to a person skilled in the art that any other arrangements of the magnet (120) to achieve the purpose of the present invention are available.

As shown in FIG. 3, more than one second electrode (230) may be attached to the outer surface of the second tube (210) with covering the tube (210) face, and the second electrode (230) may be arranged in a row at regular intervals along longitudinal direction of the second tube (210). This arrangement of more than one second electrode (230) in a separate create is not to obstruct the curve adjustment of the second tube (210) when several electrodes (230) are arranged to the outer surface of the second tube (210). In other words, the arrangement of more than one second electrode (230) in a row at regular intervals along longitudinal direction of the second tube (210) does not obstruct to bend the flexible first tube. The second electrode (230) works with the first electrode (130) of the magnetic catheter (100) to create transmural lesions with contacting the myocardial tissue to be treated (see FIG. 4).

Meanwhile, there is no limitation on the number, size, and arranged interval of the second electrode (230) and these factors may be determined by the result of preclinical trial like the first electrode (130). Further, in order the second electrode (230) to work efficiently, it is preferred that the size and arranged interval of the second electrode (230) be the same to those of the first electrode (130) of the magnetic catheter (100). In order to create transmural lesions at a treated region without gap, the preferable size and arranged interval of the second electrode (230) is 10 mm and 4 mm respectively (see FIG. 3). Any other size and arranged interval of the second electrode (230) may be available. However, too bigger size and too smaller arranged interval may obstruct the curve adjustment of the second tube (210).

On the contrary to this, transmural lesions with gap could be created when the size is below 10 mm and the arranged interval is above 4 mm. The preferable number of the second electrode (230) is 4, however, the number can be adjusted to the use of the catheter according to the present invention.

The working catheter (200) may comprise a connector (240) for the second electrode (see FIG. 1). The second electrode connector (240) is connected to each second electrode (230) by an electric wire (241) arranged in the second tube (210) (see FIG. 3). When the procedure is performed, the second electrode connector (240) is connected to the radiofrequency generator (300) and thus the second electrode (230) is connected to the radiofrequency generator (300).

The function of the second electrode connector (240) is to input radiofrequency electric currents produced by the radiofrequency generator (300) to the second electrode (230) and transfer the electric signal produced by the second electrode (230) into the radiofrequency generator (300). Finally, radiofrequency electric currents produced by the radiofrequency generator (300) are delivered to the first electrode (130) of the magnetic catheter (100) and the second electrode (230) of the working catheter (200) through the first electrode connector (140) and the second electrode connector (240), and thus, the myocardial tissue between two electrodes is heated to 70° C.-100° C. This heat causes the myocardial tissue necrosis, therefore, transmural lesions are created.

Figure 8:
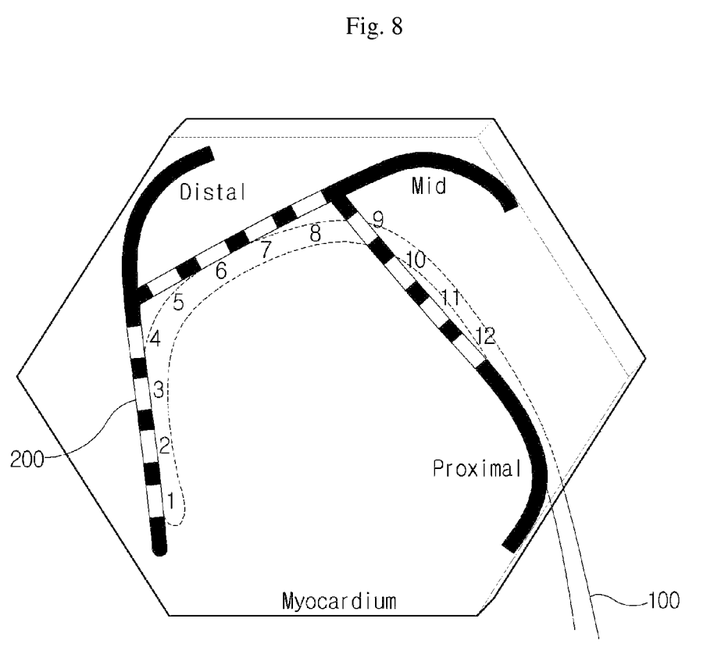
FIG. 8 is an exemplary view illustrating a mode of procedure using the bipolar radiofrequency ablation catheter according to the present invention.

Meanwhile, FIG. 8 is an exemplary view illustrating the mode of procedure using the bipolar radiofrequency ablation catheter according to the present invention. Specifically, the magnetic catheter (100) is positioned at a treated region. In order to create linear lesions from no. 1 electrode to no. 12 electrode at the treated area, the working catheter (200) is positioned at the location covered by no. 1 electrode through no. 4 electrode of the magnetic catheter (100), and the myocardial tissue is pressed between two catheters. Further, radiofrequency electric currents are delivered to the treated region (Distal). In the case that electromagnets are used as magnets (120) of the magnetic catheter (100), the electromagnets should be "on" before the myocardial tissue is pressed. When the treatment is done on the treated region, two catheters are separated and the working catheter is moved to the location of no. 5 through no. 8 electrodes of the magnetic catheter (100), and the previous method is repeated (Mid). In the case that electromagnets are used as magnets (120) of the magnetic catheter (100), the electromagnets should be "off" to separate two catheters. The region of no. 5 through no. 8 electrodes is treated as the same method (Proximal).

The following example shows that the radiofrequency ablation catheter according to the present invention has much better efficacy for creating transmural lesions than conventional catheters (unipolar or bipolar).

EXAMPLE 1

Comparison of the Efficacy for Creating a Transmural Lesion

This experiment was performed to explore the efficacy of a magnetically-coupled bipolar catheter (MB) of the present invention in comparison with conventional unipolar (UA)or bipolar (BA) radiofrequency ablation catheters.

Neodymium magnets assembled in ablation catheters were used to facilitate tissue contact in a bipolar radiofrequency ablation system. In vitro sheets of porcine skeletal muscle with 10-mm thickness were ablated with a unipolar RF ablation catheter (UA), bipolar ablation system using a pair of catheters (BA), and magnetic bipolar system (MB) according to the present invention. One side of a skeletal-muscle sheet was exposed to saline with 37° C. and flow of 37 cm/sec mimicking LV endocardial surface. Another side of a sheet was exposed to air with same temperature mimicking epicardial surface. Five ablation lesions were created in each condition. Ablated tissues were fixed with 10% formalin and lesion dimensions were measured. The results were described in Table 1.

TABLE 1

| Group | UA | BA | MB |
|---|---|---|---|
| Transmurality (%) | 0 | 0 | 40 |
| Lesion volume (mm$^3$) | 77.6 ± 19.7 | 224 ± 51.8 | 380 ± 65.3 |
| Maximum tissue temperature (° C.) | 59 ± 7.2 | 58 ± 3.8 | 58 ± 5.5 |

As shown in Table 1, even if there is no significant difference in maximum tissue temperature, the magnetically-coupled bipolar radiofrequency ablation catheter (MB) according to the present invention increased adhesive force to the myocardial region, and thus, created more transmural lesions and larger lesion volume than the conventional unipolar (UA) or bipolar (BA) catheter. Specifically, the conventional unipolar and bipolar catheters showed 0% of transmurality, while magnetically-coupled bipolar catheter according to the present invention showed 40% of transmurality. In addition, the lesion volume created by MB was over 5 times larger than that by UA, and over 1.5 times larger than that by BA.

Taken together, it is clear that the magnetically-coupled bipolar radiofrequency ablation catheter according to the present invention can easily create a larger transmural lesion at a thick myocardial region in comparison with a conventional radiofrequency ablation catheter. Specifically, in the magnetic bipolar system according to the present invention, the working catheter is pulled toward the magnetic catheter by magnetic force produced by the magnet in the magnetic catheter, and thus, two catheters press each other. Therefore, adhesive force to a treated myocardial region is increased and thus larger transmural lesions are easily created.

It is understood to a person skilled in the art that the above description of the present invention is susceptible to various modifications, changes and adaptations, and the same are intended to be comprehended within the meaning and range of equivalents of the appended claims. Therefore, the embodiments and attached drawings disclosed in the present invention are not intended to limit the technical spirit of the present invention, but are intended to describe the invention. The technical spirit of the present invention is not limited to such embodiments and drawings.

What is claimed is:

1. A bipolar radiofrequency ablation catheter comprising a magnetic catheter and a working catheter
    wherein the magnetic catheter comprises a first tube, at least two magnets, at least two first electrodes and a first electrode connector; and
    the working catheter comprises a second tube, at least two metallic elements, at least two second electrodes and a second electrode connector;
    wherein the magnets in the first tube are arranged in a row at regular intervals along the full length of a longitudinal direction of the first tube and the metallic elements in the second tube are arranged in a row at regular intervals along the full length of a longitudinal direction of the second tube;
    wherein the number, size, and spacing interval of the magnets is the same as those of the corresponding metallic elements; and
    wherein the magnets are connected by a thin and flexible string or thread and the metallic elements are connected by a thin and flexible string or thread.

2. The bipolar radiofrequency ablation catheter according to claim 1, wherein the at least two magnets are permanent magnets or electromagnets.

3. The bipolar radiofrequency ablation catheter according to claim 2, wherein at least one of the at least two magnets is an electromagnet.

4. The bipolar radiofrequency ablation catheter according to claim 3, wherein the magnet catheter additionally comprises an electromagnet connector.

5. The bipolar radiofrequency ablation catheter according to claim 4, wherein the electromagnet connector is connected to a magnetic controller.

6. The bipolar radiofrequency ablation catheter according to claim 5, wherein electric currents to the electromagnet are provided/blocked through the electromagnet connector by switching on/off the magnetic controller.

7. The bipolar radiofrequency ablation catheter according to claim 1, wherein the working catheter is pulled toward the magnetic catheter by magnetic force produced by the at least two magnets in the magnetic catheter.

8. The bipolar radiofrequency ablation catheter according to claim 1, wherein the at least two magnets and the at least two first electrodes of the magnetic catheter interact with the at least two metallic elements and the at least two second electrodes of the working catheter, respectively, by magnetic force produced by the magnet.

9. The bipolar radiofrequency ablation catheter according to claim 1, wherein the at least two first electrodes are attached to the outer surface of the first tube in a row at regular intervals along longitudinal direction of the first tube covering the tube, and the at least two second electrodes are attached to the outer surface of the second tube in a row at regular intervals along longitudinal direction of the second tube covering the tube.

10. The bipolar radiofrequency ablation catheter according to claim 9, wherein the size and arranged interval of the first electrodes are the same to those of the at least two second electrodes.

11. The bipolar radiofrequency ablation catheter according to claim 10, wherein the size of the at least two first and at least two second electrodes is 10 mm, and the arranged interval of them is 4 mm.

12. The bipolar radiofrequency ablation catheter according to claim 9, wherein 12 or more first electrodes are attached.

13. The bipolar radiofrequency ablation catheter according to claim 9, wherein 4 second electrodes are attached.

14. The bipolar radiofrequency ablation catheter according to claim 1, wherein the at least two first electrodes and the at least two second electrodes are connected to a radiofrequency generator by the first electrode connector and the second electrode connector, respectively.

15. A bipolar radiofrequency ablation catheter comprising:
    (a) a magnetic catheter which comprises a flexible hollow first tube, at least two magnets arranged in the inner side of the first tube in a row at regular intervals along the full length of a longitudinal direction of the first tube, at least two first electrodes attached to the outer surface of the first tube in a row at regular intervals along longitudinal direction of the first tube, and a first electrode connector connected to each first electrode by an electric wire for each first electrode arranged in the first tube; and
    (b) a working catheter which comprises a flexible hollow second tube, at least two metallic elements arranged in the inner side of the second tube in a row at regular intervals along the full length of a longitudinal direction of the second tube, at least two second electrodes attached to the outer surface of the second tube in a row at regular intervals along longitudinal direction of the second tube, and a second electrode connector connected to each second electrode by a distinct electric wire for each second electrode arranged in the second tube;
    wherein the number, size, and spacing interval of the magnets is the same as those of the corresponding metallic elements; and
    wherein the magnets are connected by a thin and flexible string or thread and the metallic elements are connected by a thin and flexible string or thread.

16. The bipolar radiofrequency ablation catheter according to claim 15, wherein the first and second electrode connectors are connected to a radiofrequency generator.

17. The bipolar radiofrequency ablation catheter according to claim 15, wherein the number, size, and arranged interval of the at least two magnets are the same to those of the at least two metallic elements, and the size and interval of the at least two first electrodes are the same to those at least two of the second electrodes.

18. A bipolar radiofrequency ablation catheter comprising:
    (a) a magnetic catheter which comprises a flexible hollow first tube, at least two electromagnets arranged in the inner side of the first tube in a row at regular intervals along the full length of a longitudinal direction of the first tube, at least two first electrodes attached to the outer surface of the first tube in a row at regular intervals along longitudinal direction of the first tube, a first electrode connector connected to each first electrode by an electric wire arranged in the first tube, and an electromagnet connector connected to each electromagnet by a distinct electric wire for each electromagnet arranged in the first tube and finally connected to a magnetic controller to control on/off of the electromagnet; and (b) a working catheter which comprises a flexible hollow second tube, at least two metallic elements arranged in the inner side of the second tube in a row at regular intervals along the full length of a longitudinal direction of the second tube, at least two second electrodes attached to the outer surface of the second tube in a row at regular intervals along longitudinal direction of the second tube, and a second electrode connector connected to each second electrode by a distinct electric wire for each second electrode arranged in the second tube;

wherein the number, size, and spacing interval of the magnets is the same as those of the corresponding metallic elements; and wherein the magnets are connected by a thin and flexible string or thread and the metallic elements are connected by a thin and flexible string or thread.

* * * * *